United States Patent
Rivron et al.

(10) Patent No.: US 9,303,245 B2
(45) Date of Patent: Apr. 5, 2016

(54) SELF-ASSEMBLING TISSUE MODULES

(75) Inventors: Nicolas Clément Rivron, Juvisy sur orge (FR); Jeroen Rouwkema, HR Zwolle (NL); Roman Truckenmuller, Flein (DE); Séverine Le Gac, ormesson s/marne (FR); Clemens Antoni Van Blitterswijk, HE Ruigahuizen (NL); Erik Jacob Vrij, EM Enschede (NL)

(73) Assignee: Universiteit Maastricht, Maastricht (NL)

( * ) Notice: Subject to any disclaimer, the term of this patent is extended or adjusted under 35 U.S.C. 154(b) by 731 days.

(21) Appl. No.: 12/999,841

(22) PCT Filed: Jun. 22, 2009

(86) PCT No.: PCT/NL2009/050368
§ 371 (c)(1),
(2), (4) Date: Mar. 14, 2011

(87) PCT Pub. No.: WO2009/154466
PCT Pub. Date: Dec. 23, 2009

(65) Prior Publication Data
US 2011/0171712 A1    Jul. 14, 2011

(30) Foreign Application Priority Data
Jun. 20, 2008  (EP) .................................. 08158652

(51) Int. Cl.
*C12N 13/00* (2006.01)
*C12N 5/00* (2006.01)
(Continued)

(52) U.S. Cl.
CPC .............. *C12N 5/0062* (2013.01); *C12N 5/069* (2013.01); *C12N 5/0663* (2013.01); *C12N 5/0691* (2013.01); *C12N 2533/52* (2013.01); *C12N 2533/54* (2013.01)

(58) Field of Classification Search
None
See application file for complete search history.

(56) References Cited

U.S. PATENT DOCUMENTS

| 5,792,653 A | 8/1998 | Weibezahn et al. |
|---|---|---|
| 2002/0072117 A1* | 6/2002 | Xu et al. .................. 435/366 |
| 2009/0018033 A1* | 1/2009 | Morgan et al. ............... 506/26 |

FOREIGN PATENT DOCUMENTS

| WO | WO 2007/115337 | * 10/2007 | ............... C12N 5/08 |
|---|---|---|---|
| WO | 2009/154466 A1 | 12/2009 | |

OTHER PUBLICATIONS

Khademhosseini et al., Lab Chip, 5:1380-1386 (2005).*
(Continued)

*Primary Examiner* — Blaine Lankford
*Assistant Examiner* — Thomas J Visone
(74) *Attorney, Agent, or Firm* — TraskBritt

(57) ABSTRACT

The invention relates to a new approach to constructing cellular aggregates in vitro and their use in methods for producing 3D-tissue constructs in a modular way.
In particular, the invention is directed to a method for in vitro producing a tissue construct comprising:
a) combining living cells to form supracellular aggregates using spatial confinement;
b) combining two or more of the supracellular aggregates in a mold or on a biomaterial;
c) applying conditions that induce self-assembly within the combined supracellular aggregates to obtain the tissue construct; and
d) applying conditions that induce tissue morphogenesis in the tissue construct.

27 Claims, 10 Drawing Sheets

Figure 1:
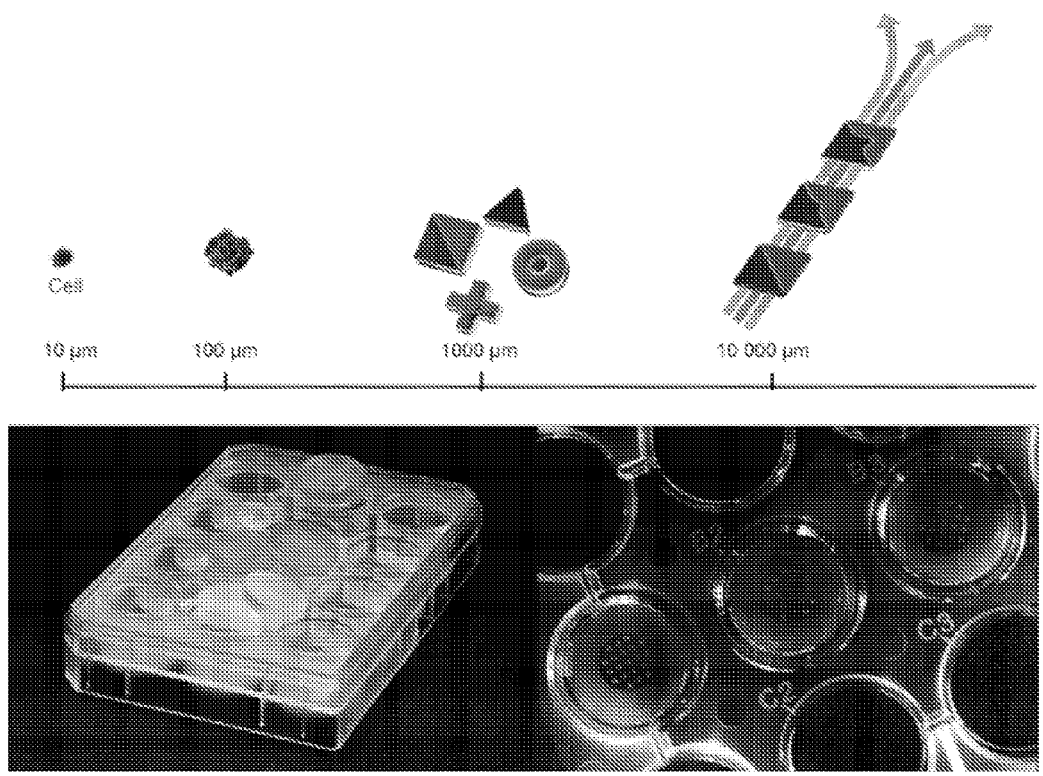

(51) Int. Cl.
*C12N 5/071* (2010.01)
*C12N 5/0775* (2010.01)

(56) References Cited

OTHER PUBLICATIONS

Moeller et al., Biomater., 29:752-763 (2008).*
Yamada et al., Stem Cells, 25:562-570 (2005).*
Ungrin et al., Plos One, 3(2):1-12 (2008).*
Karp et al., Lab Chip, 7:786-794 (2007).*
Wang et al (Biotechnol. Prog., 22:811-818 (2006).*
Sauer et al. (JCB, 75:710-723 (1999).*
Caspi et al., Circ. Res., 100:263-272 (2007).*
Guo et al., Meth. Enzy., 420:316-338 (2006).*
Guo et al., Circ., 113:2229-2237 (2006).*
Kisiday et al., J. Biomech., 37:595-604 (2004).*
Terraciano et al., Stem Cells, 25:2730-2738 (2007).*
Mauck et al., J. Biomeech. Eng., 122(3):252-260, abstract (2000).*
Rosenthal et al., Biomater., 28(21):3208-3216 (2007).*
Caspi et al., Circ Res., 100:263-272 (2007).*
Napolitano et al., "Dynamics of the Self-Assembly of Complex Cellular Aggregates on Micromolded Nonadhesive Hydrogels." Tissue Engineering 13: 2087-2094, 2007.
Kelm et al., "Design of Custom-Shaped Vascularized Tissues Using Microtissue Spheroids as Minimal Building Units." Tissue Engineering 12: 2151-2160, 2006.
Jakab et al., "Tissue Engineering by Self-Assembly of Cells Printed into Topologically Defined Structures." Tissue Engineering 14: 413-421, 2008.
Sodunke et al., "Micropatterns of Matrigel for three-dimensional epithelial cultures." Biomaterials 28: 4006-4016, 2007.
Moeller et al., "A microwell array system for stem cell culture." Biomaterials 29: 752-763, 2008.
International Search Report issued in PCT/NL2009/050368 and dated Sep. 25, 2009.

* cited by examiner

A

B

A

B

A

B

C

D

E

F

A

B

C

SELF-ASSEMBLING TISSUE MODULES

CROSS-REFERENCE TO RELATED APPLICATIONS

This application claims the benefit of European Patent Application No. 08158652.1 filed Jun. 20, 2008 and International Application No. PCT/NL2009/050368 filed Jun. 22, 2009, the contents of each of which are incorporated herein by reference.

The invention relates to a new approach to constructing cellular aggregates of defined sizes and shapes in vitro and their use in methods for producing 3D-tissue constructs in a modular way.

Most tissues consist of multiple cell types organized with specific microscale heterogeneity. Typically, one cubic centimeter can hold up to 300 million cells. These cells form different structures within the tissue, including blood capillaries and a neural network, which are crucial for nutrition, innervation and homeostasis of the tissue. Cells organize and interact in a multitude of architectures and synthesize a variety of biologically active molecules for mechanical support and cellular instruction. Therefore, living tissues are highly complex.

Tissue engineering is a term used for attempts to produce living tissue in vitro from individual or groups of cells. It aims at repairing or replacing portions of or whole tissues and provides solutions to shortage of organ donation or to the use of experimental animals for testing new therapies.

Due to the high complexity of living tissue, efforts to produce or mimic living tissues in vitro have been in vain to date and new methods and technologies to assemble cells into tissue structures are needed. This is currently a main limitation in disciplines like regenerative medicine, pharmaceutics, oncology and developmental biology in which 2D culture and crude small 3D cell aggregates (see e.g. WO-A-00/75286) are still standards. As a result, biological in vitro experiments do not even come close to complex biological reality, research progress is severely inhibited, and experimental animals have to be used as an unsatisfactory experimental alternative instead.

With the recent developments in both adult and embryonic stem cell biology, it is becoming truly feasible to induce cells in culture into more and more of the individual cell types that are found in the human body and in spectacular high numbers.

Unfortunately, a satisfactory technology to go from a large pool of cells including different cell types to a tissue mimic with a complex architecture has not yet been developed. Several possible strategies, such as organ printing (see e.g. WO-A-2005/081971) and cell sheet technology, are currently being explored. These strategies rely heavily on the possibility to position (pools of) cells in a predefined organization. These strategies are encountering obstacles that prevent the translation of a complex architecture to an actual centimeter scale tissue (i.e. remodeling of the tissue construct over time due to physical shrinkage or cell migration). Furthermore, the rationale behind organ printing is still beyond reach of contemporary science as it simply requires too many ($10^8$) single steps. Even at a, currently unattainable, speed of depositing one thousand individual cells per second at the right three dimensional location, with micrometer accuracy, it would take close to four days to build a single cubic centimeter of tissue. These approaches and related technologies result in a metastable multicellular construct: the construct is not stable but will remodel according to complex biological principles. This means that with these strategies, a designed structure and complexity is not translated to the objective tissue. Promoting the self-assembly and self-organization of pools of cells is thus a more powerful approach. In this approach, cells are assembled into a construct prone to a predictable remodeling overtime. Under appropriate boundary conditions the construct leads to a final organized tissue. This is achieved by using a bottom-up approach to sequentially assemble cells into, subsequently, supracellular aggregates and tissues and by promoting the self-organization of the tissue using boundary conditions.

Several attempts to assemble cells into tissues using a bottom up approach are already described which are different from the presented invention. McGuigan and Sefton (*PNAS* 2006, 103 (31), 11461-11466) have undertaken an attempt to overcome these practical difficulties by starting from microscale modular components, consisting of submillimeter-sized collagen gel rods seeded with endothelial cells into a microvascularized tissue. These modules were manually assembled into a larger tube and perfused by medium or blood. However, their approach requires the use of a gel, in this case a collagen gel, to obtain the modules and retain their structural integrity during the subsequent manual assembly into larger structures. Although the use of a gel can be advantageous in some cases to control for instance cell density, the entrapment of cells within a gel will decrease the plasticity of the modules and prevent fusion between modules. Eliminating the necessity to use gels for the formation of tissue modules allows for more plasticity and physiological remodeling of the tissue during the self-assembly process. Sodunke et al. (*Biomaterials* 2007, 28 (27), 4006-4016) describe a similar approach based on a biomatrix hydrogel. Gels have the disadvantages in that the interface is not available and in that the cells have low movability.

An early attempt to generate gel-free cellular aggregates for use as building blocks to construct bigger tissues has been described by Kelm et al. (*Tissue Eng.* 2006, 12 (9), 2541-2553). This attempt is based on the so-called "hanging drop"-method, wherein cells in an inverted drop of tissue culture medium precipitate and aggregate. However, this method cannot generate sufficiently large numbers of cellular aggregates in a short enough time. Conventional methods for producing multicellular models (such as the hanging drop method or micromass culture) suffer from a number of limitations including (i) a poor control of size and shape of the aggregates, and reproducibility, (ii) tedious and time-consuming manipulations (iii) low production yield of microtissues. Napolitano et al. (*Tissue engineering* 2007, 13 (8), 2087-2095) describe a method to form cellular aggregates by self-assembly on micromolded non-adhesive hydrogels. This document does not describe the formation of pre-condensed cellular aggregates in a first step and subsequent self-assembly of the cellular aggregates as building blocks in a second step. This method thus induces intense and non-predictable remodeling (e.g. shrinking) of the tissue construct.

The invention aims at overcoming one or more of these problems by producing supracellular aggregates of cells of any cell type using spatial confinement. These aggregates are used as building blocks and combined using boundary conditions promoting their self-assembly and self-organization to create complex multicellular architectures.

In a first aspect, the invention relates to a method for in vitro producing a tissue construct comprising:
a) combining living cells to form supracellular aggregates using spatial confinement;
b) combining two or more of the supracellular aggregates in a mold or on a biomaterial;

c) applying conditions that induce self-assembly within the combined supracellular aggregates to obtain the tissue construct; and
d) applying conditions that induce tissue morphogenesis in the tissue construct.

The invention provides various advantages over prior art methods, including the use of simple tools that can be handled in most biology labs, the ability to generate a very large amount of aggregates in quick and simple procedure (e.g. 220 000 aggregates per conventional 12 well plate), and the absence of a hydrogel as supporting material.

The spatial confinement can be achieved in various manners. A well-known and often applied way is by using arrays of microwells. Other ways of imposing spatial confinement include using air-liquid interfaces like the Hanging drop method or microfluidic channels. Any biocompatible, processable material can be used for the spatial confinement applied for assembling the cells into supracellular aggregates.

The term "microwell" as used in this application is meant to refer to an array of numerous cup-like structures formed in a substantially uniform layer of material by photolithographic patterning, molding, embossing or other manufacturing processes. Each microwell thus includes a lower wall (which may be formed by a substrate on which the microwell material is deposited) and one or more peripheral side walls (e.g. a single circular wall, or three or more contiguous substantially straight walls) that extend upward from the bottom wall and surround a predefined lower wall area, with upper edges of the peripheral side walls defining an open end of the microwell. Typically, microwells having an enveloping diameter of 50-500 µm can be used. The depth of the microwells is normally in the range of 100-1000 µm. For seeding it is advantageous that individual microwells are close to each other in order to prevent cells staying on the spaces between the microwells. Thus, the maximum distance between two individual neighboring microwells on the array can for example be 300 µm or less, preferably 200 µm or less, more preferably 100 µm or less, such as about 50 µm. The number of microwells in the array can vary depending on the size of the microwells and the distance between individual microwells. One array can suitably have 50-20 000 wells, such as 50-5000, or 100-2000 wells.

The term "self-assembly" as used in this application is meant to refer to the creation of tissue units (or small building units) by association of individual cells or cellular aggregates. The individual cells or cellular aggregates adhere together in specific arrangements to give one-dimensional, two-dimensional or three-dimensional superstructures. The aggregation may be spontaneous without human intervention, or may be as a result of changing local environmental conditions, e.g. temperature, concentration of cells, physical boundaries (such as specific shape or dimension of the microwells and/or mold), etc.

In a first step, a method according to the invention comprises producing a supracellular aggregate of cells. These cells may be of the same ("homocellular") or different ("heterocellular") type within one aggregate. It is preferred, however, that one aggregate is formed of cells of one cell type. Diversification of the tissue construct to be produced may be achieved by combining aggregates of different cell types.

Many cell types may be used to form the cell aggregates. In general, the choice of cell type will vary depending on the type of three dimensional construct to be built. For example, for a blood vessel type three dimensional structure, the cell aggregates will advantageously comprise a cell type or types typically found in vascular tissue (e.g. endothelial cells, smooth muscle cells, etc.). In contrast, the composition of the cell aggregates may vary if a different type of construct is to be produced (e.g. intestine, liver, kidney, etc.). One skilled in the art will thus readily be able to choose an appropriate cell type for the aggregates, based on the objective type of three-dimensional construct. Non-limiting examples of suitable cell types include contractile or muscle cells (e.g. striated muscle cells and smooth muscle cells), neural cells, connective tissue (including bone, cartilage, osteoblasts, osteoclasts, cells differentiating into bone forming cells and chondrocytes, and lymph tissues), hepatocytes, cardiomyocytes, myocytes, Schwann cells, urothelial cells, parenchymal cells, epithelial cells (including endothelial cells that form linings in cavities and vessels or channels, exocrine secretory epithelial cells, epithelial absorptive cells, keratinizing epithelial cells, and extracellular matrix secretion cells), and undifferentiated cells (such as embryonic cells, progenitor cells, (mesenchymal) stem cells, bone marrow cells, satellite cells, fibroblasts, and other precursor cells), among others. Also plant cells and algae may suitably be used.

The aggregates may vary in both size and shape. They may for example be in the form of a sphere, a cylinder (preferably with equal height and diameter), a rod, a cube, or the like. Although other shaped aggregates may be used, it is generally preferable that the cell aggregates are spherical, cylindrical (with equal height and diameter), or cuboidal (i.e. cubes), as aggregates of these shapes may be easier to manipulate. The shape of the cellular aggregates can play an important role in promoting self-assembly. Different shapes of aggregates can generate different arrangements by stacking. The shapes of the cellular aggregates can for instance promote close proximity between cellular aggregates (e.g. key-lock system), or create free space at their interfaces. Aggregates are substantially uniform in size and substantially uniform in shape when they are combined but different shapes and sizes can be assembled to generate different heterogeneous structures.

Although the exact number of cells per aggregate is not critical, it will be recognized by those skilled in the art that the size of each aggregate (and thus the number of cells per aggregate) is limited by the capacity of nutrients to diffuse to the central cells, and that this number may vary depending on cell type. Cell aggregates may comprise a minimal number of cells (e.g. two or three cells) per aggregate, or may comprise many hundreds or thousands of cells per aggregate. Typically, cell aggregates comprise hundreds to hundreds of thousands of cells per aggregate.

The number of cells in one aggregate can be controlled by the applied spatial confinement. For instance, the number of cells in one aggregate can be dependent on the number of cells that are seeded in a microwell and the size of the well. There is, however, no 1:1 ratio, because cell death and proliferation may occur during formation of the aggregate. In a suitable embodiment, the number of cells that is provided per microwell is 2-500 000, such as 100-100 000, or 100-50 000. Furthermore, the number of cells applied, e.g. per microwell, also depends on the desired aggregate size.

For purposes of the present invention, the cellular aggregates are typically from about 100 microns to about 600 microns in size, such as from about 200 to about 400 microns, although the size may be greater or less than this range, depending on cell type. In one embodiment, the cell aggregates are from about 250 microns to about 400 microns in size. In another embodiment, the cell aggregates are about 250 microns in size. For example, spherical cell aggregates are preferably from about 20 microns to about 600 microns in diameter (such as from about 100 microns to about 600 microns), cylindrical cell aggregates are preferably from about 100 microns to about 600 microns in diameter and height, and the sides of cuboidal cell aggregates are preferably from about 100 microns to about 600 microns in length. Aggregates of other shapes will typically be of similar size. The size of the aggregates can be measured using standard light microscopy techniques.

The size of the cellular aggregates can be controlled by the spatial confinement, such as by size of the microwells, as well as by the number of cells that is used, such as the number of cells seeded to the microwells. Importantly, the size of the aggregates depends more on the number of cells than on the enveloping diameter of the spatial confinement. The size and/or the shape of the spatial confinement can be roughly adjusted to facilitate proper aggregate formation. If the spatial confinement is too large, the cells will not find each other and will not aggregate. If the spatial confinement is too small, then not all cells will fit in the well. For example, for aggregates having a size between 0 and 90 µm circular microwells with a diameter of 100 microns are suitable; for aggregates having a size between 90 and 150 µm circular microwells with a diameter of 200 µm are suitable; for aggregates between 150 and 350 µm circular microwells with a diameter of 400 microns are suitable.

As mentioned above, in with a suitable embodiment of the invention aggregates of cells are produced using arrays of microwells that can be produced with technologies that include, but are not limited to: microchip technology, hot embossing, selective laser sintering, solid free-form fabrication, and phase separation micromolding. With these technologies, arrays of microwells can be produced in sheets of different materials including, but not limited to: PDMS (polydimethylsiloxane), collagen, gelatin, hydrogels, and the like. An important advantage of the abovementioned technologies is that they can produce microwells with different size and shape.

The invention considers both the use of spatial confinement with single morphology (such as arrays containing single microwell morphology) and spatial confinement with two or more morphologies (such as arrays containing two or more microwell morphologies). In an embodiment, cell aggregates are formed by applying a cell suspension on top of the microwell array. Typically, the cell concentration in the cell seed suspension is in the range of 500 000 cells per ml to 5 000 000 cells per ml. Cells either settle in the microwells spontaneously due to gravitational forces, or are forced in the microwells using for instance centrifugal, capillary forces or microfluidic devices.

Upon spatial confinement the cells will aggregate spontaneously by adhesion between the cells. The adhesion between the same cell types is not necessarily better than between different cell types, although this may be the case for some specific cell types. The adhesion between the different cells differs from cell type to cell type. For instance, human mesenchymal stem cells will form spheroids that condense a lot due to strong adhesion between the cells, HUVEC will form spheroids that hardly condense due to moderate adhesion between the cells, and Chinese hamster ovary cells will form plates in stead of spheroids due to low adhesion between the cells. Assembly of the cells into supracellular aggregates may be assisted by various tools known in the art, such as microfluidic tools, moving liquids, confining chambers with modular properties (adherent/non-adherent surfaces), using surfaces with topographies, or using surfaces with coatings.

It is important to note in this aspect that in order for aggregates to form, the adhesion between cells and the surrounding material (such as the material of the microwell) is preferably lower than the adhesion between the cells themselves. This can, for example, be achieved by using microwells of materials that display low cellular adhesion, such as PEG (polyethyleneglycol), PDMS or the like, or by coating the microwell surface with molecules that prevent cellular adhesion, such as PEG and BSA (bovine serum albumin). Moreover, it is important to note that the formation of aggregates depends on the cellular adhesion of the cell type used. When a certain cell type is unable to form cellular aggregates spontaneously, aggregation may be initiated using compounds such as fibronectin or collagen that can be added to the cell suspension.

The shape of the aggregates can be manipulated by altering the spatial confinement shape. The size of the aggregates can be manipulated by altering the size of the spatial confinement, the cell concentration of the cell suspension used, and/or the composition of the culture medium that is used during cellular aggregation.

An advantage of using microwells when compared to classical methods to produce cellular aggregates, like the hanging-drop method, is that in a single 'step' one can make thousands of aggregates at the same time, instead of merely one aggregate. This enables the fabrication of the vast quantities of aggregates that are needed for this bottom-up approach. For instance, in comparison with the spontaneous aggregation in a cell suspension, the microwells allow a precise control and reproducibility of the shape, size, and surface properties of the aggregates.

The invention is further illustrated in FIG. 1. The top scheme describes the technical steps to assemble cells into tissues with geometric steps in a bottom up approach. Cells are assembled into spheroids that are used as building blocks to build tissues. These tissues are shaped, e.g. to promote self-remodeling and can be influenced to self-organize. For example, sharp tips of a triangular tissue promote compaction of the construct inducing further developmental mechanisms. The bottom picture shows some of the tools that can be used to bring the invention into practice. Polymeric stamps can be used to replicate structures into agarose. Agarose chips can be inserted into a conventional microwell plate and used for cell and tissue culture.

The cell suspension can suitably be added to a container (for instance 12-well plate) in which an array of microwells has been placed on the bottom. The cells can then sink into the wells by gravitational or centrifugational forces. In principle the values of temperature and pH do not have to vary from the values that are used during standard culture of the respective cell types. However, there are applications foreseeable where for instance a change in temperature can be used to initiate cell aggregation. The basis for the cell suspension is normally a culture medium supplemented with standard nutrients (not different from normal cell culture). Aggregation usually takes place in a standard incubator (humidified, 37° C., 5% $CO_2$). If different cell types are used, they can be mixed in one cell suspension, or they can be applied separately, depending on the initial situation one wants to create. If both cells are mixed in one cell suspension, the different cell types will typically be regularly mixed in the resulting aggregate. If the different cell types are applied in different cell suspensions one after the other, the resulting aggregate will typically consist of two (or more) distinct regions containing the two (or more) different cell types.

It is an advantage of the invention that aggregates may be formed, that do not contain anything but living cells. In particular, the use of a gel is not necessary. This way, aggregates of particular high cell density may be formed. In some cases this can lead to a better contact between the different cells for exchange of compounds, since some cells rely on direct cell contact for cellular communication. In addition, the absence of a gel allows for the cells to better produce their own extracellular matrix in a physiological way. Furthermore, the addition of a gel from xenogenous origin may impose a complication for clinical applications. By only using autologous cells the product is completely patient-own.

Step a) allows the condensation of cells into building blocks (supracellular aggregates). This condensation process that is occurring over time is essential, since shaped microtissues cannot be produced on a large (mm) scale by seeding the cells in large wells. Condensation of the small aggregates minimizes the condensation of the bigger shapes in a later stage. If the step of forming the supracellular aggregates through condensation would be skipped, then the shape of a subsequent seeding surface (such as macro-wells) will not be translated to the desired construct. After seeding, the tissue will condense toward a spheroid, regardless of the shape of the seeding surface. Apart from that, the inventors found that pre-condensation (i.e. formation of supracellular aggregates) allows to seed a larger number of cells as aggregates (e.g. spheroids), compared to seeding a cell suspension. It is therefore necessary to first condense cells into dense building blocks (supracellular aggregates) that thereafter can be used and assembled into bigger constructs.

Thereafter, the cellular aggregates are combined to obtain larger tissue constructs. This can be described as a two-stage process.

The first stage is the self-assembly of cellular aggregates into a bigger tissue construct. In a suitable embodiment, the aggregates are removed from a microwell array by flushing (culture) medium over the surface of the microwell. Another possibility is to invert a chip with microwells onto the surface to be seeded. Aggregates are then released by gravitational or centrifugational forces and transferred to the seeding surface (e.g. biomaterial, scaffold, macro-well). For self-assembly, the aggregates can for instance be transferred into wells having an enveloping diameter of at least 500 µm. Any biocompatible, processable material can be used for the spatial confinement applied for assembling the supracellular aggregates into tissue constructs.

Self-assembly of the cellular aggregates will be governed by imposed "boundary conditions" of the cellular aggregates such as supracellular aggregate size, supracellular aggregate shape, supracellular aggregate surface properties (for instance hydrophilicity/hydrophobicity or a coating with bioactive molecules that results in specific interactions between the cellular aggregates), supracellular aggregate electrical charge, supracellular aggregate magnetic charge and of "boundary conditions" of the chamber used to assemble the cellular aggregates such as adherent or non-adherent surfaces of the chamber, topographies of the surface of the chamber, protein deposition and patterning at the surface of the chamber and the use of microfluidic to promote the arrangement and assembly of the cellular aggregates.

Preferably, the "boundary conditions" are imposed on the aggregates before they are released from the initial spatial confinement. Depending on the type of boundary condition, this may or may not require an extra active step. For instance, the boundary condition "supracellular aggregate size" is already imposed by the spatial confinement and the seeding density. The boundary condition "supracellular aggregate surface properties" can be adjusted, for instance, by coating the aggregates before releasing them from the spatial confinement. The boundary condition "supracellular aggregate magnetic charge" can be imposed during seeding (e.g. by including magnetic particles) or by coating the aggregates before releasing them from the spatial confinement.

After incorporating these boundary conditions to the cellular aggregates or the chamber used for their self-assembly, self-assembly of the cellular aggregates can be guided e.g. in a chamber or in a moving liquid by applying for instance mechanical constraints, shear stress using a liquid, compression, shaking, electrical fields, magnetic fields, or gradients of morphogens and/or growth factors. The shape, size and cell type(s) of the supracellular aggregates is important in the early stage of the assembly to promote mesoscale organization and create the heterogeneous structure of interest. Self-assembly of the aggregates normally takes several hours. Typically, it takes at most one day. The structure of interest can include the simple assembly of spherical aggregates into the shape of a cylinder or the more complex assembly of spherical aggregates into blocks (cubes, triangles, etc.) that can then be assembled into bigger constructs. For example, using the plastic properties of cells, chambers with compensated shapes can be designed, which result in the desired tissue construct shapes. The design and structures of those constructs should promote the creation of local environment leading to further remodeling and tissue development.

Some illustrative examples of conditions that can be used to promote self-assembly of the cellular aggregates into a tissue construct include the cell type, the medium used to culture the tissue, and the time of incubation on e.g. the microwell array before the transfer to the final chamber.

The second stage involves the remodeling and/or reorganization of the cells and/or tissue in the construct. In this stage conditions are applied that induce tissue morphogenesis in the tissue construct. The term "morphogenesis" in this application is meant to refer to a coordinated series of molecular and cellular events that shape the structure of the tissue construct. Tissue morphogenesis and can be governed by migration of cells, physical traction of cells, differentiation of cells, local production of soluble or insoluble (extra-cellular matrix) biological factors, or combinations thereof. Remodeling and/or reorganization can further involve compaction of the cells and/or tissue in the tissue construct. This second stage can be characterized as further development of the tissue construct and can again be guided by applying artificial parameters such as mechanical constraints, compression, shaking, electrical fields, magnetic fields, the action of objects embedded into the construct and subjected or not to external forces, or gradients of morphogens and/or growth factors. Typically, the combination of cellular aggregates of different sizes in a stirred liquid promotes the formation of patterned arrangements. The combination of cellular aggregates of complementary shapes promotes the formation of tissues with repetitive units.

Remodeling and/or reorganization can for instance involve applying geometrical constraints (such as using a chamber with specific geometry) to the tissue construct. This can induce self-organization into tissues (such as local compaction, local growth of capillaries).

The geometrical shape of the tissue in itself can induce local remodeling and/or reorganization of the cells, including compaction of the cells, local stress, local sprouting of endothelial cells into blood capillaries.

The cells can be assembled on chips made of biocompatible materials including agarose, PDMS or PLLA casted on etched silicone wafer by conventional lithography process or replicated by hot-embossing, polymers can be further functionalize to modify their interaction with cells using coated with polymers (e.g. PEG) or proteins (e.g. BSA), patterns of adhesive proteins promoting local adhesion of the tissue construct or nanometer and micrometer topographies. Chips are in the order of centimeter scale and fit in classical cell-culture well-plates. Wells in the order of 100 to 1500 µm (such as in the order of 500 to 1500 µm) are generated in which the aggregates can self-assemble.

Depending on the methods that are used for the self-assembly of the cells and/or cellular aggregates a wide variety of constructs shapes can be designed and prepared using the method of the invention. For instance, when using wells, in which the aggregates are combined to constructs, the shape of the wells will be translated to the shape of the construct.

Also the construct size may vary widely. However, the maximal size may be limited by the diffusion distance of oxygen and nutrients. A way to overcome this is for instance by using perfusion or superfusion systems. The constructs will normally have a size of at least 500 µm, or at least 1 mm. The upper limit of the size can for instance be 4 mm or 1.5 cm.

When combining the cell aggregates to obtain a tissue construct, self-assembly may be assisted using a biomaterial, e.g. to form a scaffold and provide mechanical support or to assist in achieving a particular desired shape. In addition, biomaterials or bio-active factors may be included that guide the development or organization of the tissue construct. Types of biomaterials that can be incorporated include, but are not limited to: ceramics, bioglasses, polymeric materials (biodegradable or non-biodegradable), metals, gels. Types of bio-active factors that can be incorporated include, but are not limited to: enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA. Biodegradable object and/or metallic objects are preferred. It is possible to combine the object with living cells, to combine the object with supracellular aggregates, and/or to combine the object with tissue constructs. The object can thus be introduced in steps, a) or b) and/or in steps c) or d). Metallic objects can be used to modify the cellular aggregate or tissue by using an electrical or magnetic field.

An important aspect of the invention is that the aggregates, after having been combined, will self-assemble into biological tissues, which may vary in complexity. To this end, aggregates of different cell types are preferably combined. Aggregates of the cell types that make up a tissue may be combined to replicate said tissue. Features to incorporate in tissues may include, but are not limited to, a vascular network (endothelial cells and smooth muscle cells/pericytes), a neural network (neural cells), a lymphatic network (lymphatic endothelial cells). For instance for skeletal muscle tissue, aggregates of skeletal muscle cells, neural cells, endothelial cells, smooth muscle cells/pericytes, and lymphatic endothelial cells may be combined.

Without wishing to be bound by theory, it is postulated that the self-assembly of the aggregates into tissue structures (also referred to as tissue morphogenesis) can be caused by migration of cells, physical traction or compaction of cells, local production of soluble or insoluble (extra-cellular matrix) biological factors, differentiation of cells, or combinations thereof.

The obtained tissue constructs can be used for various applications. They can for instance serve as a platform for creating constructs for tissue repair, or as a platform for studying tissue development (as a scientific tool), as an in vitro test model for compound testing in pharmacology or cosmetics, etc. The invention will now be further elucidated by way of the following, non-restrictive examples.

EXAMPLES

Figure 2:
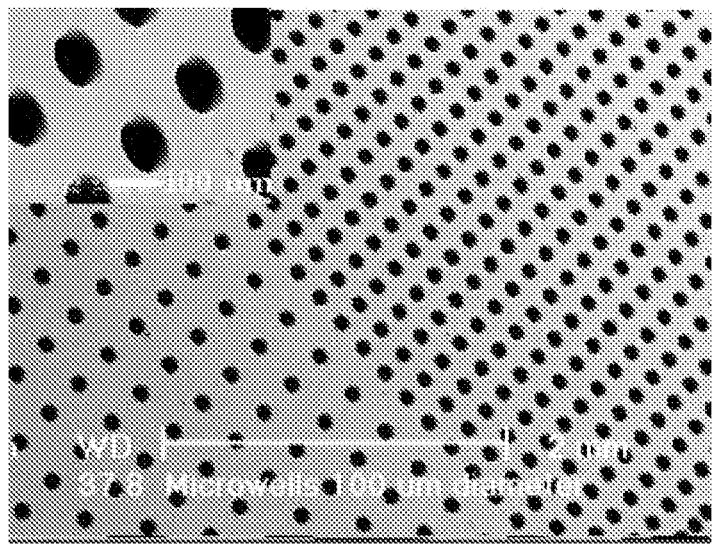
Figure 3:
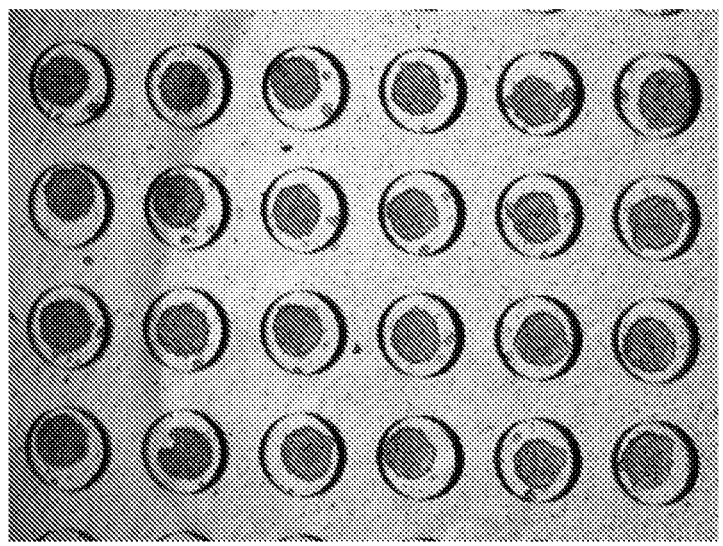

The microdevice shown in FIG. 2, consisting of an array of microwells of various dimensions (well diameter, spacing and depth) fabricated in PDMS, was used for the spontaneous and simultaneous formation of a number of microscale spheroids, in a fast, controlled and reproducible way (see FIG. 3). Aggregate formation is straightforward and requires reduced amounts of cells and biological factors. The size of the microtissues is tunable (~25 to 100 000 cells) and more suitable for imaging purposes. We have firstly studied the optimal properties of the material i.e. giving little/no cellular adherence and strong cellular aggregation for the preparation of spheroids based on hMSCs (human Mesenchymal Stem Cells) or HUVECs (Human Umbilical Vein Endothelial Cells), and we have notably investigated the PDMS composition (curing agent:base ratio) in combination with various coatings. Both parameters greatly influence cellular adherence and aggregation. The results range from strong to no adherence on the surface, and cellular assembly from isolate cell "suspension" to extensive cell aggregation. Best efficiency in the formation of spheroids is observed with a coating of 35 000 MW PEG and a 10:0.5 PDMS composition. PDMS 10:0.5 gives the smallest cellular adherence and 35 000 MW PEG at a concentration of 50 mg/ml promotes cellular aggregation (see Table 1). The resulting spheroids exhibit a size in the hundreds of micron range depending on the size of the microwells and the cell seeding density, see FIG. 4.

Figure 7:
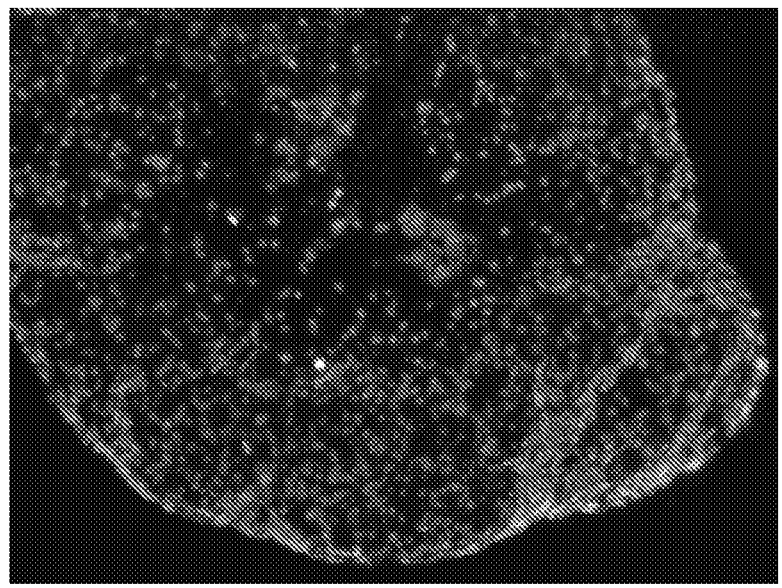
Figure 7:
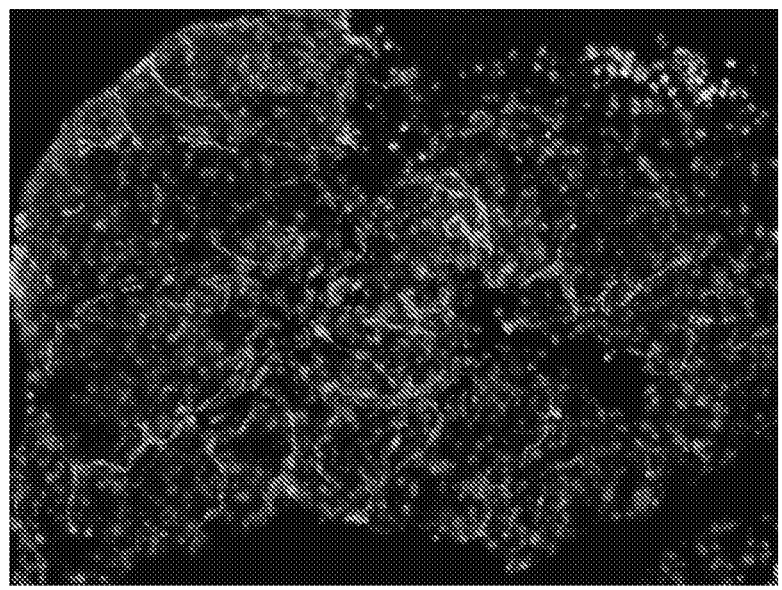

Cellular aggregates can then be harvested and assembled into different shapes, and different cell types can be combined. Here we present the case of the assembly of hMSC and HUVEC aggregates into an agarose mold. The mold is made by replication of agarose on a stainless steel master (1×1×10 mm), see FIG. 5. 5 000 cellular aggregates of each cell type were combined into this mold. They self assembled into a stratified tube with a layer of HUVEC surrounding a core of hMSC (FIG. 7). This self-assembly process is due to the differential surface tension of the two types of aggregates promoting segregation. Over time, the construct will remodel according to biological processes of angiogenesis and lead to a vascularized cylinder of dense tissue.

TABLE 1

Preparation of microtissues in coated PDMS-based microwells: Cellular aggregation and adherence on the surface depending on the PDMS composition and the coating nature.

| PDMS composition | Ø | Fibronectin | Coating BSA 10 mg/ml | BSA 50 mg/ml | PEG 300 10 mg/ml | PEG 35 000 50 mg/ml | Agarose |
|---|---|---|---|---|---|---|---|
| 10:0.5 | Adherence: + | Adherence: + | Adherence: --- | Adherence: +++ | Adherence: - | Adherence: No | Adherence: No |
|  | Aggregation: + | Aggregation: ++ | Aggregation: -- | Aggregation: ++ | Aggregation: + | Aggregation: +++ | Aggregation: --- |

TABLE 1-continued

Preparation of microtissues in coated PDMS-based microwells: Cellular aggregation and adherence on the surface depending on the PDMS composition and the coating nature.

| PDMS composition | Coating | | | | | | |
|---|---|---|---|---|---|---|---|
| | Ø | Fibronectin | BSA 10 mg/ml | BSA 50 mg/ml | PEG 300 10 mg/ml | PEG 35 000 50 mg/ml | Agarose |
| 10:1 | Adherence: -- <br> Aggregation: -- | Adherence: - <br> Aggregation: +++ | Adherence: --- <br> Aggregation: -- | Adherence: +++ <br> Aggregation: +++ | Adherence: --- <br> Aggregation: - | Adherence: + <br> Aggregation: +++ | Adherence: --- <br> Aggregation: --- |
| 10:3 | Adherence: +++ <br> Aggregation: ++ | Adherence: +++ <br> Aggregation: + | Adherence: - <br> Aggregation: +++ | Adherence: +++ <br> Aggregation: + | Adherence: + <br> Aggregation: + | Adherence: + <br> Aggregation: + | Adherence: ++ <br> Aggregation: ++ |

In FIG. 7, human mesenchymal stem cell from bone marrow and human umbilical vein endothelial cells were separately cultured and aggregated onto chips. The chips are made of PDMS coated with 50 mg/ml BSA. The microwells on the chip are 200 microns diameter and 300 microns deep. Cells were allowed to aggregate into spheroids during 24 hours. hMSC are cultured in DMEM+glutamax, 100 nM dexamethasone (Sigma), 1% Pen/Strep (100 U/100 µg/ml, GIBCO), 50 mg/ml ITS-plus Premix (BD), 50 µg/ml ascorbic acid (Sigma), 40 µg/ml proline (Sigma), 100 µg/ml sodium pyruvate (Sigma). HUVEC are grown and aggregated in EGM2 medium (Lonza).

5 000 spheroids of each cell type (10 000 spheroids total) were transferred to an agarose chip with one trench (1 mm width, 1 mm depth and 1 cm long). This agarose (4%) is molded on a stainless steel mold.

The 10 000 spheroids quickly aggregated and formed a cylindrical tissue construct. This construct was cultured for 6 days and sectioned and immunostained at day 3 and 6 for CD31 and Dapi.

A self-assembly of the two cell types in two concentric layers was observed at day 3 where the HUVEC are forming an external layer and the hMSC an internal core. This was followed by an invasion of the HUVEC into the centre of the construct on day 6 and the formation of a primitive capillary network.

Figure 8:
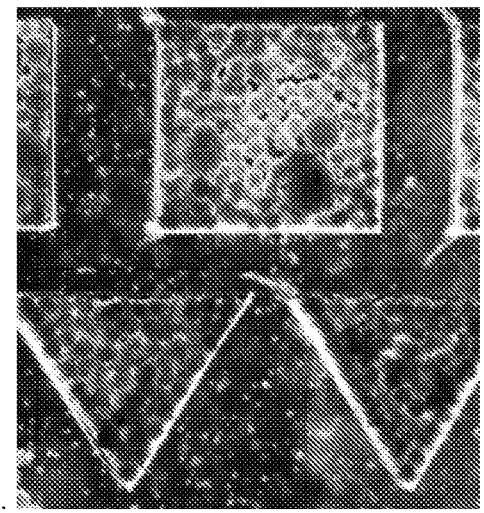
Figure 8:
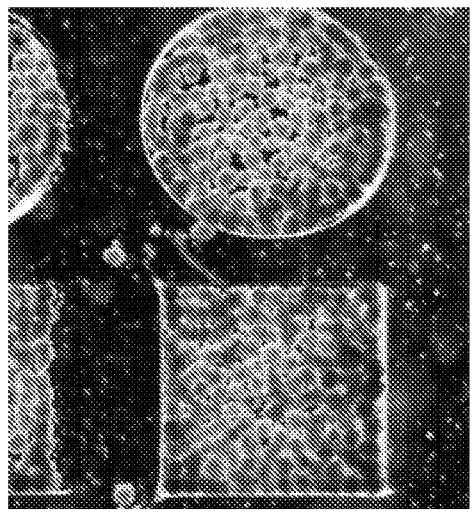
Figure 8:
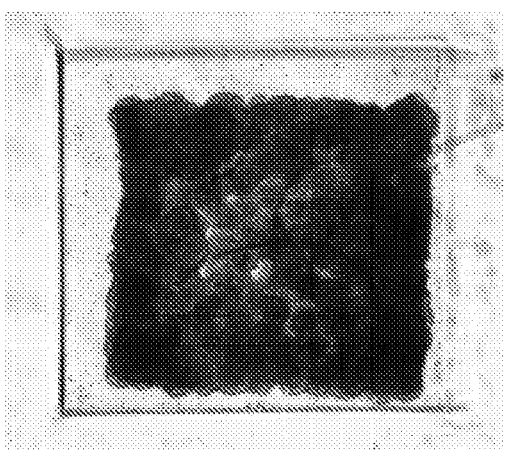
Figure 8:
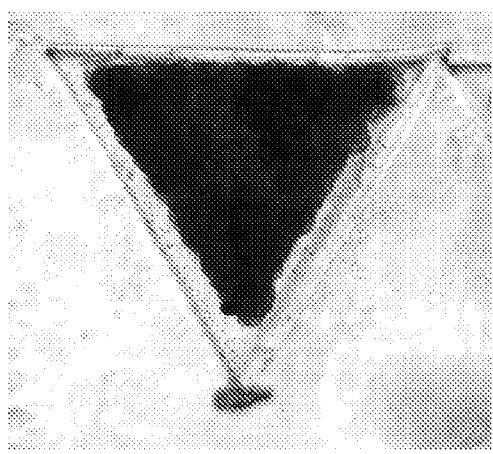
Figure 8:
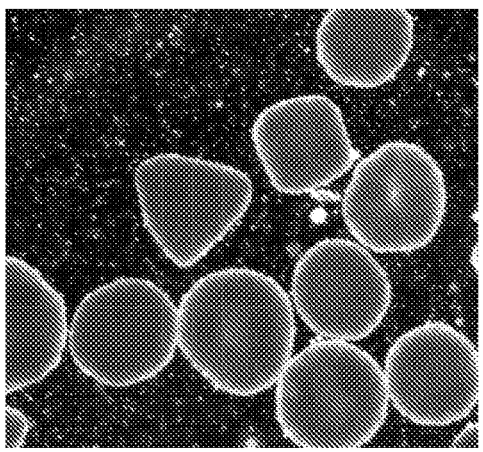
Figure 8:
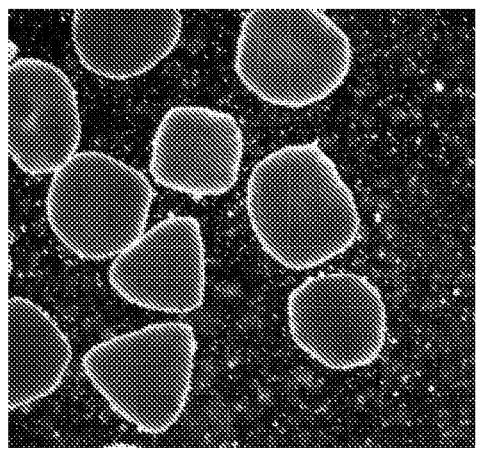

In FIG. 8, spheroids of hMSC were produced as described above. 15 000 spheroids of 100 microns diameter were transferred onto an agarose chip with wells of different shapes (i.a. squares, triangles and circles). The agarose chip (4% agarose) is molded on a PDMS mold. The wells have a total surface area of 0.64 mm² and a depth of 1 mm. The spheroids were seeded onto the chip and formed mesoscale tissue of defined size and shape. Those mesoscale tissues were harvested after 24 hours and can be combined and used to built tissue models or tissue implants.

FIG. 9A shows that the size of the building blocks depends on the number of cells seeded and on the size of the microwells. Using human mesenchymal stem cells and two different sizes of microwells (200 and 400 µm), building blocks from 30 to 150 µm were assembled. In FIG. 9B it is shown that also different culturing media can induce different levels of compaction. Furthermore, as shown in FIG. 9C, different cell types show different plasticity and maintenance of the shape over time. This plasticity decreased with longer incubation on the microwells array. For each cell type and each culturing medium, a time of incubation on the microwells array has to be adjusted.

Figure 10:
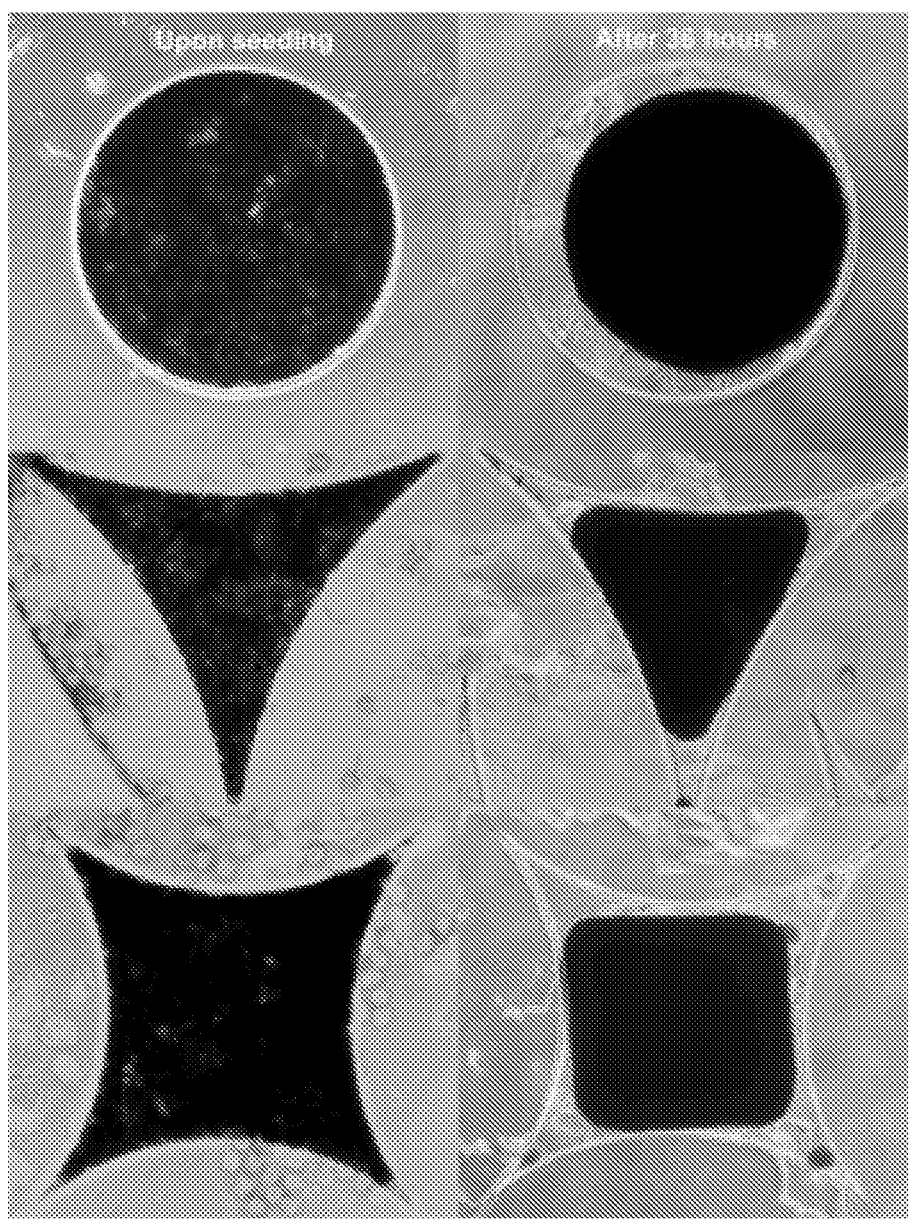
Figure 11:
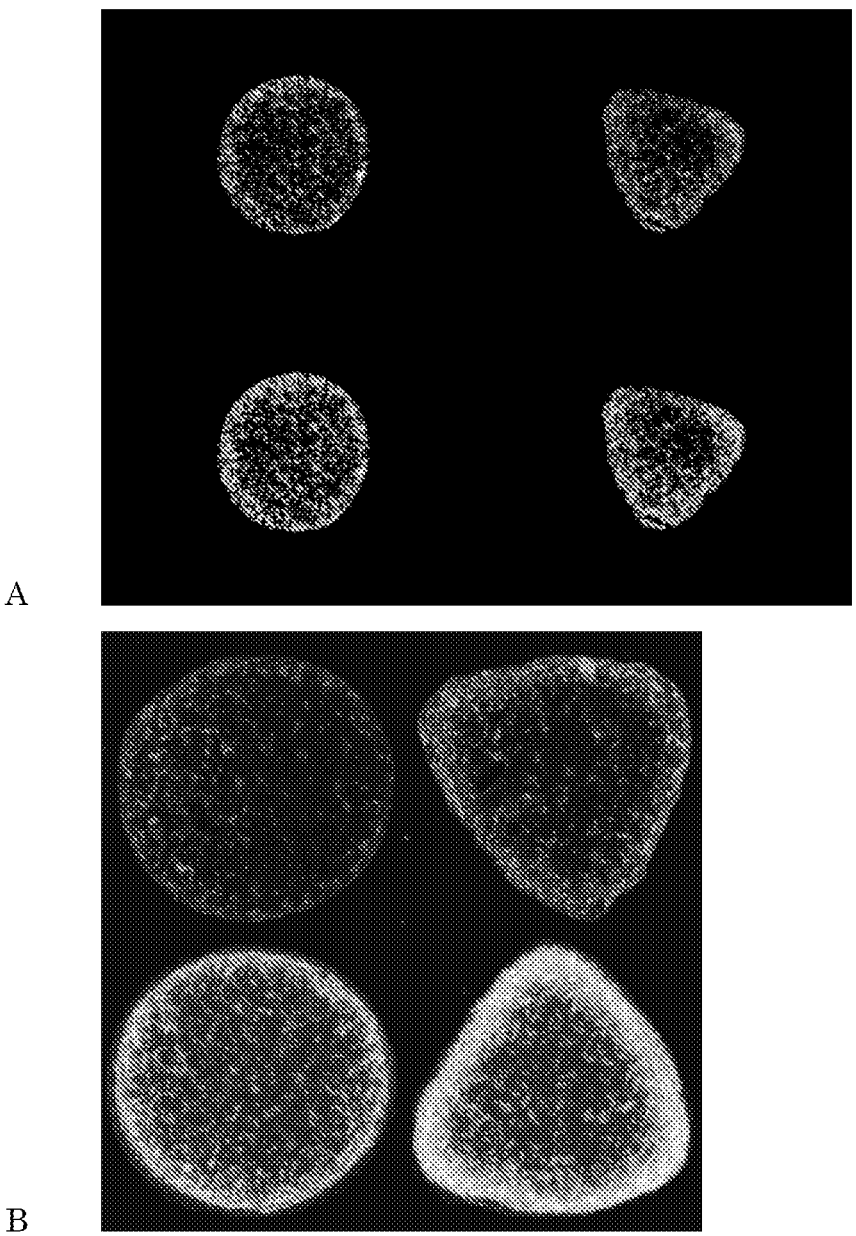

FIG. 10 shows that compaction of the tissue construct is not uniform for all shapes. Corners are regions of greater compaction. Compensated shapes can be designed to promote remodeling of the tissue into a desired geometry In FIG. 11 it is shown that both the local compaction and the local stress of the tissue depends on the geometrical shape. FIG. 11A shows a nuclear staining of 7 µm cuts. A local compaction of the cells (nuclei are closer to each other) was observed on the outside of tissues compared to the inside in discs (left pictures) and tip effects with local cell compaction in the tips of triangular tissues (right pictures). FIG. 11B shows a cytoskeleton staining of 7 µm cuts. Regions of more intense F-actin populations of cells were observed. The shape of the tissues created local microenvironments of stress.

Figure 12:
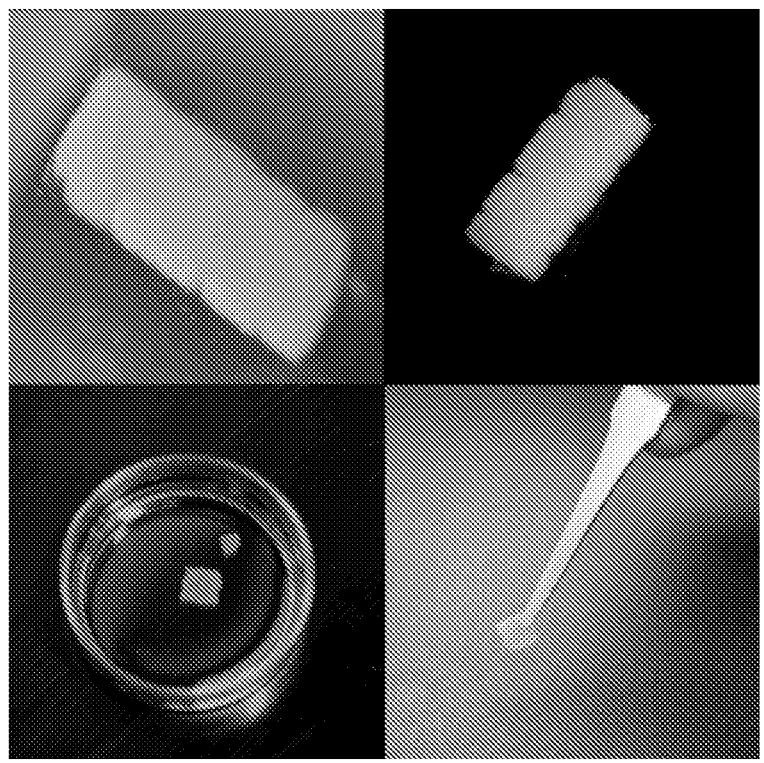

As can be seen from FIG. 12, further assembling into tissues of clinically relevant size (such as centimeter-scale) is possible. Tissues spontaneously fuse and can be manipulated thus achieving clinical relevance.

FIG. 1. Top: illustrative scheme of the invention.
Bottom: tools that can be used to bring the invention into practice.

FIG. 2. SEM picture of a microwell array (diameter 100 µm, depth 350 µm) for the spontaneous formation of microtissues. In insert, enlarged view of wells molded in PDMS.

FIG. 3. Spheroids prepared from HUVECs cells in a PDMS microsystem (10:0.5) coated with 35 000 MW PEG at 50 mg/ml. Microwells are of 200 µm diameter and 350 µm depth.

Figure 4:
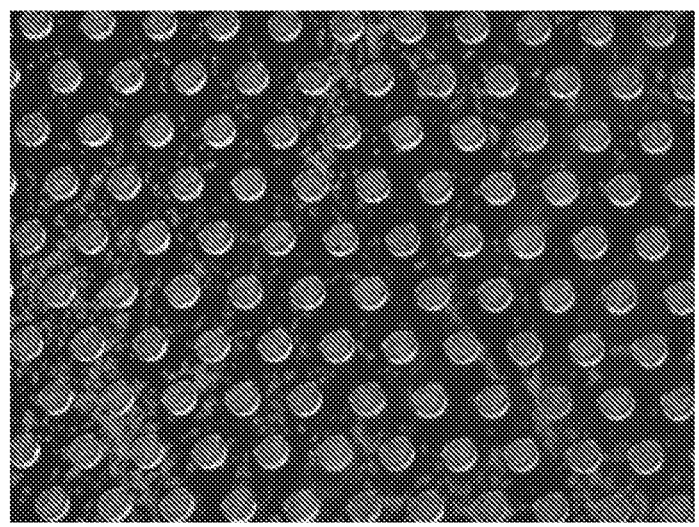
Figure 4:
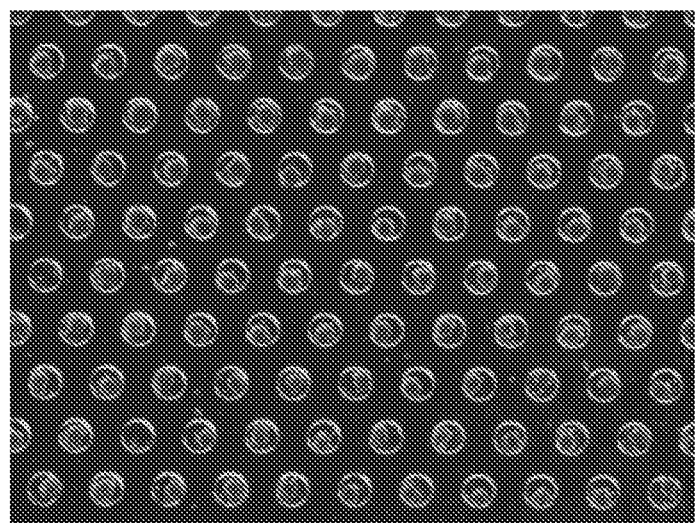

FIG. 4. Spheroids prepared from human bone marrow derived mesenchymal progenitor cells in a PDMS microsystem (10:0.5) coated with 35 000 MW PEG at 50 mg/ml. Microwells are of 200 µm diameter and 350 µm depth. Picture A is taken just after seeding and picture B after 2 days of culture.

Figure 5:
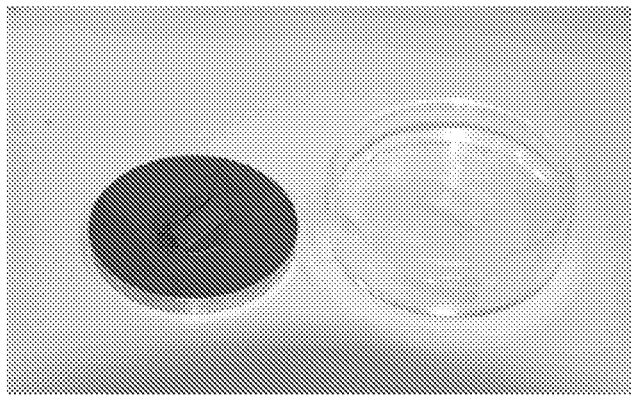

FIG. 5. Stainless steel mold (left) used as a master to replicate an agarose chamber (right) used to assemble aggregates.

Figure 6:
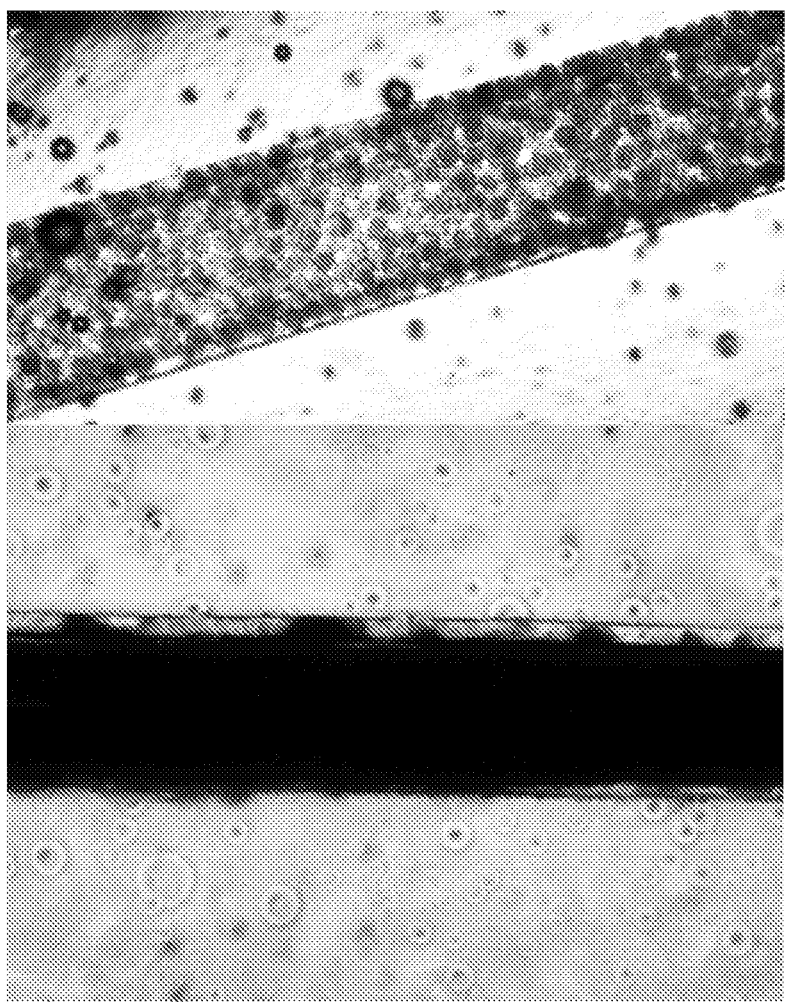

FIG. 6. Aggregates of HUVEC and hMSC assembled into the agarose chamber just after seeding after 3 days of culture. The width of the chamber is 1 mm, the depth of the chamber is 1 mm and the length of the chamber is 1 cm.

FIG. 7. Self-assembly of aggregates of different cell types. Cross section of cylinder described previously after 3 days (A) and 6 days (B). On day 3, one can observe the segregation of cell types with the HUVEC, in red, forming an exterior layer. After 6 days, the angiogenesis processes took place and capillaries are formed in the tissue construct.

FIG. 8. Cellular aggregates of hMSC can be assembled into tissue constructs of different shapes to built tissue units that can then be assembled into bigger constructs. Panels A and B: 15 minutes after seeding the aggregates. Panels C and D: 5 hours after seeding the aggregates. Panels E and F: tissue constructs were released from the wells, 24 hours after seeding the aggregates.

Figure 9:
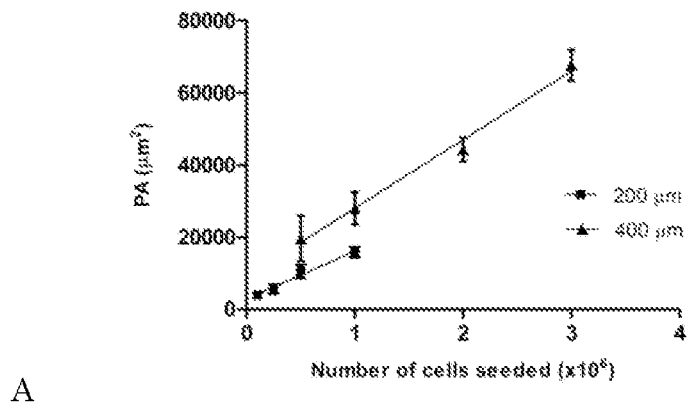
Figure 9:
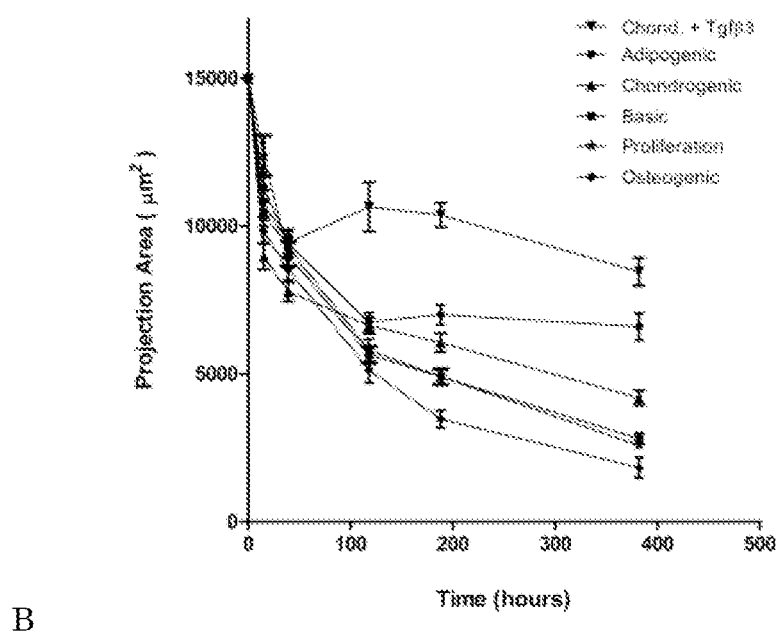
Figure 9:
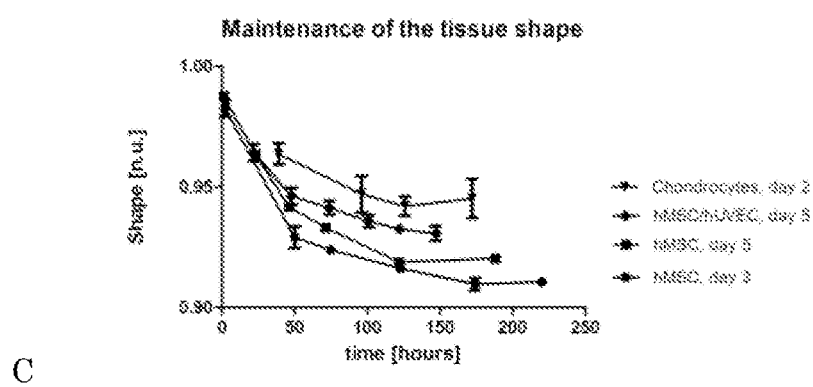

FIG. 9 A The size of the building blocks depends on the number of cells seeded and on the size of the microwells.

B Different compositions of culturing media induce different levels of compaction of the spheroids over time.

C Different cell types show different plasticity and maintenance of the shape over time.

FIG. 10 Remodeling of the tissue construct into a desired geometry by using compensated shapes.

FIG. 11 A Local compaction of the tissue depends on the geometrical shape.

B Local stress of the tissue depends on the geometrical shape.

FIG. 12 Tissues can further be assembled into centimeter-scale tissues.

The invention claimed is:

1. A method for in vitro producing a tissue construct which substantially retains its shape after release from a well, the method comprising:
   a) combining living cells to form supracellular aggregates using spatial confinement by condensation of said cells in microwells having an enveloping diameter in the range of 50 μm to 500 μm into supracellular aggregates;
   b) combining two or more of the supracellular aggregates in a mold or biomaterial comprising a well having a geometric shape and having enveloping diameter of at least 100 μm;
   c) applying conditions that induce self-assembly within the combined supracellular aggregates to obtain the tissue construct;
   d) applying conditions that induce tissue morphogenesis in the tissue construct; and
   e) releasing the tissue construct from the well,
   wherein the condensation of step a) allows the tissue construct to maintain at least 90% of its non-spherical shape for 150 hours has after said release of the tissue construct from the well having a geometric shape as compared to the shape of the construct while still within the well having geometric shape.

2. The method according to claim 1, wherein said tissue morphogenesis comprises migration and/or differentiation of cells.

3. The method according to claim 1, wherein step (a) further comprises incubating the supracellular aggregates in said microwells having a depth in the range of 100-1,000 μm, and adjusting the duration of said incubation, thereby adjusting the plasticity of the formed supracellular aggregates during said self-assembly.

4. The method according to claim 1, wherein the microwells have a shape that is different from a cylinder.

5. The method according to claim 4, wherein the shape of at least some of the microwells is such that the resulting aggregates can self-assemble according to the lock-and-key principle.

6. The method according to claim 1, wherein 2-500,000 cells per microwell are combined to form a supracellular aggregate.

7. The method according to claim 1, wherein the living cells are of the same cell type and are combined to form the supracellular aggregates.

8. The method according to claim 1, wherein the cells are selected from the group consisting of endothelial cells, smooth muscle cells, striated muscle cells, neural cells, connective tissue cells, osteoblasts, osteoclasts, chondrocytes, hepatocytes, cardiomyocytes, myocytes, Schwann cells, urothelial cells, parenchymal cells, epithelial cells, exocrine secretory epithelial cells, epithelial absorptive cells, keratinizing epithelial cells, extracellular matrix secretion cells, or undifferentiated cells, such as embryonic cells, progenitor cells, (mesenchymal) stem cells, bone marrow cells, satellite cells, fibroblasts, and other precursor cells.

9. The method according to claim 1, wherein the supracellular aggregates have a mean particle size of 20-400 μm as measured by light microscopy.

10. The method according to claim 1, wherein the biomaterial is selected from the group consisting of ceramics, bioglasses, biodegradable polymeric materials non-biodegradable polymeric materials, and metals.

11. The method according to claim 1, wherein the array of microwells is prepared by microchip technology, hot embossing, selective laser sintering, solid free-form fabrication, or phase separation micromolding.

12. The method according to claim 1, wherein the array of microwells comprises at least two microwells having a substantially different size and/or shape.

13. The method according to claim 1, wherein the microwells are made of agarose, PEG (polyethyleneglycol) or PDMS.

14. The method according to claim 1, wherein the microwell surface is coated with one or more compounds capable of reducing and/or preventing cellular adhesion, selected from the group consisting of polyethylene glycol and bovine serum albumin.

15. The method according to claim 1, wherein the living cells are combined in the presence of fibronectin and/or collagen.

16. The method according to claim 1, wherein the surface properties, the magnetic charge, and/or the electrical charge of the supracellular aggregates are modified before combining two or more of the supracellular aggregates.

17. The method according to claim 1, wherein the supracellular aggregates are combined in a in a microfluidic chamber and/or microfluidic channel.

18. The method according to claim 1, wherein the conditions in step c) comprise one or more selected from mechanical constraints, compression, shaking, electrical fields, magnetic fields, and gradients of morphogens or growth factors.

19. The method according to claim 1, wherein in step a) or b) the living cells or the supracellular aggregate is combined with an object and/or wherein in step c) or d) the tissue construct is combined with a metallic material and/or a polymeric material, to induce a local response.

20. The method according to claim 1, wherein the method further comprises remodeling the tissue construct into a desired geometry by utilizing a well having a geometry that compensates for relatively greater compaction in the corners of the well.

21. The method according to claim 1, wherein the method further comprises a step of assembling the non-spherical tissue construct in centimeter scale tissues.

22. The method according to claim 1, wherein in step (d) the tissue morphogenesis-inducing conditions include local deformation, compaction of the tissue construct and subsequent local biological changes resulting in spatial heterogeneity by applying geometrical constraints to the tissue construct.

23. The method according to claim 1, wherein in step (d) the conditions that induce tissue morphogenesis include self-deformation of the tissue construct.

24. The method according to claim 1, wherein the well having a geometric shape in step (b) is a cylinder or blocks in the form of cubes or triangles and wherein self-assembly of the aggregates in step (c) is into the cylinder or blocks in the form of cubes or triangles such that when releasing the tissue construct from the well, the tissue construct have the non-spherical shape of the cylinder or the blocks in the form of cubes or triangles.

25. The method according to claim 7, wherein a first type of supracellular aggregates of a first cell type is combined with a second type of supracellular aggregates of a second cell type, and wherein said first and second cell type are different from each other.

26. The method according to claim 25, wherein the first cell type is HUVEC (Human Umbilical Vein Endothelial Cells) and the second cell type is hMSC (human Mesenchymal Stem Cells), and combining at least 5000 supracellular aggregates of HUVEC and at least 5000 supracellular aggregates of hMSC in a single well in the shape of a trench in step b), to form a cylindrical tissue construct comprising a primitive capillary network formation.

27. The method according to claim 1, wherein the microwell array is formed of a PDMS (polydimethyelsiloxane) composition comprising from 10:0.5 to 10:1 mass ratio of base to current agent, coated with a coating of more than 10 mg/ml of BSA (Bovine Serum Albumin) or a coating of more than 10 mg/ml of 35,000 molecular weight PEG.

* * * * *